(12) United States Patent
Lee et al.

(10) Patent No.: US 12,297,159 B2
(45) Date of Patent: May 13, 2025

(54) PREPARATION PROCESS OF 5-ETHYLIDENE-2-NORBORNENE

(71) Applicant: KOREA KUMHO PETROCHEMICAL CO., LTD., Seoul (KR)

(72) Inventors: Young Rok Lee, Daejeon (KR); Jae Woo Kim, Daejeon (KR); Kyoung Ho Row, Daejeon (KR); Ick Jin An, Daejeon (KR); Jin Woo Park, Daejeon (KR); Yu Mi Kim, Cheonan-si (KR)

(73) Assignee: KOREA KUMHO PETROCHEMICAL CO., LTD., Seoul (KR)

( * ) Notice: Subject to any disclaimer, the term of this patent is extended or adjusted under 35 U.S.C. 154(b) by 66 days.

(21) Appl. No.: 18/324,487

(22) Filed: May 26, 2023

(65) Prior Publication Data
US 2024/0076252 A1    Mar. 7, 2024

(30) Foreign Application Priority Data

May 30, 2022  (KR) .................. 10-2022-0066034
Sep. 2, 2022  (KR) .................. 10-2022-0111503
(Continued)

(51) Int. Cl.
*C07C 13/20* (2006.01)
*B01J 21/04* (2006.01)
(Continued)

(52) U.S. Cl.
CPC .............. *C07C 13/20* (2013.01); *B01J 21/04* (2013.01); *B01J 37/04* (2013.01); *B01J 37/08* (2013.01); *C07C 2521/04* (2013.01)

(58) Field of Classification Search
CPC . C07C 13/20; C07C 2521/04; C07C 2523/04; C07C 2601/10; C07C 2602/42;
(Continued)

(56) References Cited

U.S. PATENT DOCUMENTS 4,219,688 A * 8/1980 Ogawa ...................... C07C 2/50
                                              585/366
4,538,013 A * 8/1985 Donike ...................... C07C 2/50
                                              526/83
(Continued)

OTHER PUBLICATIONS

Ji Hee Oh et al., "Isomerization of 5-Vinyl-2-norbornene Using Sodium-coated Catalysts", Bull. Korean Chem. Soc., 2008, vol. 29, No. 11, pp. 2202-2204 (4 pages total).

*Primary Examiner* — Ali Z Fadhel
(74) *Attorney, Agent, or Firm* — Suchrue Mion. PLLC

(57) ABSTRACT

A preparation process of 5-ethylidene-2-norbornene, including: introducing dicyclopentadiene into a dicyclopentadiene decomposition reactor to thermally decompose the dicyclopentadiene; introducing a product of the above step into a cyclopentadiene purification tower; introducing 1,3-butadiene, a solvent, and cyclopentadiene separated from the top of the cyclopentadiene purification tower into a Diels-Alder reactor to react the same; introducing a product of the immediate above step into a 1,3-butadiene removal tower to recover 1,3-butadiene from the top; introducing a mixture at the bottom of the 1,3-butadiene removal tower into a desolvation tower, and recycling a solvent and unreacted raw materials recovered from the top of the desolvation tower to the dicyclopentadiene decomposition reactor; introducing a mixture at the bottom of the desolvation tower into a 5-vinyl-2-norbornene separation tower to separate 5-vinyl-2-norbornene; and introducing the 5-vinyl-2-norbornene into an isomerization reactor to react the same.

20 Claims, 5 Drawing Sheets

(30) Foreign Application Priority Data

Sep. 2, 2022 (KR) .......................... 10-2022-0111504
May 24, 2023 (KR) .......................... 10-2023-0066802

(51) Int. Cl.
*B01J 37/04* (2006.01)
*B01J 37/08* (2006.01)

(58) Field of Classification Search
CPC ........... C07C 5/2512; C07C 4/22; C07C 2/50;
C07C 7/04; B01J 21/04; B01J 37/04;
B01J 37/08
See application file for complete search history.

(56) References Cited

U.S. PATENT DOCUMENTS

| | | | | |
|---|---|---|---|---|
| 4,777,309 | A * | 10/1988 | Kimura | C07C 2/50 |
| | | | | 526/75 |
| 5,565,069 | A * | 10/1996 | Oi | C07C 4/22 |
| | | | | 585/366 |
| 6,294,706 | B1 * | 9/2001 | Bergstrom | C07C 13/68 |
| | | | | 526/75 |
| 2002/0156334 | A1 * | 10/2002 | Seo | C07C 13/61 |
| | | | | 585/360 |
| 2009/0054714 | A1 * | 2/2009 | Bell | C07C 7/148 |
| | | | | 585/363 |
| 2011/0137094 | A1 * | 6/2011 | Ammannati | C07C 7/20 |
| | | | | 585/315 |

* cited by examiner (a)      (b)      (c)      (d)

PREPARATION PROCESS OF 5-ETHYLIDENE-2-NORBORNENE

CROSS-REFERENCE TO RELATED APPLICATION

This application claims priority to and the benefit of Korean Patent Application No. 10-2022-0066034, filed on May 30, 2022, Korean Patent Application No. 10-2022-0111503, filed on Sep. 2, 2022, Korean Patent Application No. 10-2022-0111504, filed on Sep. 2, 2022 and Korean Patent Application No. 10-2023-0066802, filed on May 24, 2023, the entire disclosures of which are incorporated herein by reference in its entirety.

BACKGROUND

1. Field of the Invention

This specification relates to a preparation process of 5-ethylidene-2-norbornene.

2. Discussion of Related Art

5-Ethylidene-2-norbornene (ENB) is a raw material for an ethylene-propylene-diene monomer (EPDM), and is a highly functional special synthetic rubber mainly used for automobile parts due to its excellent heat resistance, ozone resistance and chemical resistance.

5-Ethylidene-2-norbornene can be prepared through an isomerization reaction of 5-vinyl-2-norbornene (VNB) using a base catalyst, and in a 5-ethylidene-2-norbornene preparation process, dicyclopentadiene (DCPD) may be used as a raw material.

Dicyclopentadiene is a dimer compound of cyclopentadiene (CPD), is produced as a by-product during cracking of naphtha obtained from crude oil, and is included at 10 to 20% by weight in a C5 fraction having hydrocarbons having 5 carbon atoms as a main component or C9+ fractions having hydrocarbons having 9 or more carbon atoms as a main component in the by-product stream. That is, the dicyclopentadiene can be obtained by separation from cracker by-product streams such as the C5 fraction or C9+ fractions.

Dicyclopentadiene can be decomposed into cyclopentadiene through thermal decomposition, and 5-vinyl-2-norbornene may be prepared by reacting cyclopentadiene, which is a thermal decomposition product, with 1,3-butadiene through a Diels-Alder reaction. Thereafter, 5-ethylidene-2-norbornene may be prepared by isomerization of 5-vinyl-2-norbornene.

In order to improve the economic feasibility of the 5-ethylidene-2-norbornene preparation process, it is necessary to increase the separation/purification efficiency of each process involved in the 5-ethylidene-2-norbornene preparation process and to minimize raw material loss.

SUMMARY OF THE INVENTION

The description of the present specification is to solve the problems of the related art described above, and one object of the present specification is to provide a preparation process of 5-ethylidene-2-norbornene with excellent process efficiency.

According to one aspect, the present invention provides a preparation process of 5-ethylidene-2-norbornene, including: step a-1 of introducing dicyclopentadiene (DCPD) into a DCPD decomposition reactor (110) to thermally decompose the DCPD; step a-2 of introducing a product of step a-1 into a cyclopentadiene (CPD) purification tower (120); step b-1 of introducing 1,3-butadiene (BD), a solvent, and cyclopentadiene separated from the top of the CPD purification tower (120) into a Diels-Alder reactor (210) to react the same; step b-2 of introducing a product of step b-1 into a BD removal tower (220) to recover 1,3-butadiene from the top; step b-3 of introducing a mixture at the bottom of the BD removal tower (220) into a desolvation tower (230), and recycling a solvent and unreacted raw materials recovered from the top of the desolvation tower (230) to the DCPD decomposition reactor (110); step c of introducing a mixture at a bottom of the desolvation tower (230) into a 5-vinyl-2-norbornene (VNB) separation tower (300) to separate 5-vinyl-2-norbornene; and step d of introducing the 5-vinyl-2-norbornene into an isomerization reactor (410) to react the same.

In one embodiment, the VNB separation tower (300) may include a first VNB separation tower (310) and a second VNB separation tower (320), and the step c may include step c-1 of introducing the mixture at the bottom of the desolvation tower (230) into the first VNB separation tower (310) to introduce a mixture separated from the top of the first VNB separation tower (310) into the second VNB separation tower (320), and step c-2 of separating 5-vinyl-2-norbornene from the bottom of the second VNB separation tower (320).

In one embodiment, the mixture separated from the top of the first VNB separation tower (310) may include 5-vinyl-2-norbornene and 4-vinyl-cyclohexene (VCH).

In one embodiment, the 4-vinyl-cyclohexene may be separated from the top of the second VNB separation tower (320).

In one embodiment, the preparation process may further include step e of introducing a mixture at the bottom of the first VNB separation tower (310) into a DCPD recovery tower (510) to recycle materials recovered from a top of the DCPD recovery tower (510) into the DCPD decomposition reactor (110).

In one embodiment, the materials recovered from the top of the DCPD recovery tower (510) may include dicyclopentadiene and 3a,4,7,7a-tetrahydroindene (THI).

In one embodiment, the 3a,4,7,7a-tetrahydroindene may be separated from a bottom of the CPD purification tower (120).

In one embodiment, step a-1 may be a step of introducing dicyclopentadiene into the DCPD decomposition reactor (110) and thermally decomposing the dicyclopentadiene in the presence of an inert gas.

In one embodiment, in step b-1, a molar ratio of cyclopentadiene and 1,3-butadiene introduced into the Diels-Alder reactor (210) may range from 1:2 to 1:4.

In one embodiment, step d may include step d-1 of filling the isomerization reactor (410) with a catalyst; and step d-2 of introducing the 5-vinyl-2-norbornene into the isomerization reactor (410) to react the same.

In one embodiment, the catalyst may be a catalyst in which an alkali metal or alkaline earth metal is supported on a surface of a basic support.

In one embodiment, the catalyst may be a solid catalyst prepared by a method including: step 1 of heat-treating a basic support; step 2 of mixing the heat-treated basic support with an alkali metal or alkaline earth metal to obtain a mixture; and step 3 of heat-treating the mixture.

In one embodiment, the catalyst may be a solid catalyst slurry prepared by a method further including step 4 of inputting the solid catalyst into at least one solvent selected from the group consisting of heptane, toluene, and paraffin oil.

In one embodiment, the basic support may satisfy at least one of the following conditions (i) to (iii): i) a pH of 8.5 to 11; (ii) an average particle diameter of 30 to 500 pin; and (iii) a BET specific surface area of 150 to 250 m²/g.

In one embodiment, step 1 may be performed at 150 to 500° C., step 2 may be performed at a temperature of 20 to 80° C. or more compared to a melting point ($T_m$) of the alkali metal or alkaline earth metal, and step 3 may be performed at a temperature of 50 to 150° C. or more compared to the melting point ($T_m$) of the alkali metal or alkaline earth metal.

In one embodiment, a weight of the alkali metal or alkaline earth metal relative to a volume of the basic support may be 0.05 to 0.5 g/mL.

In one embodiment, steps 1 to 3 may be performed under conditions of an oxygen concentration of 100 ppm or less.

In one embodiment, a temperature of the isomerization reactor (410) in step d-2 may be maintained at 10 to 50° C., and a space velocity of the 5-vinyl-2-norbornene may be 5.0/h or less.

In one embodiment, the space velocity of the 5-vinyl-2-norbornene may be 2.0/h or less.

In one embodiment, step d may further include step d-3 of inputting a spent catalyst used in the reaction into at least one solvent selected from the group consisting of heptane, toluene, and paraffin oil to obtain a spent catalyst slurry; and step d-4 of inputting water to the spent catalyst slurry to oxidize the catalyst.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
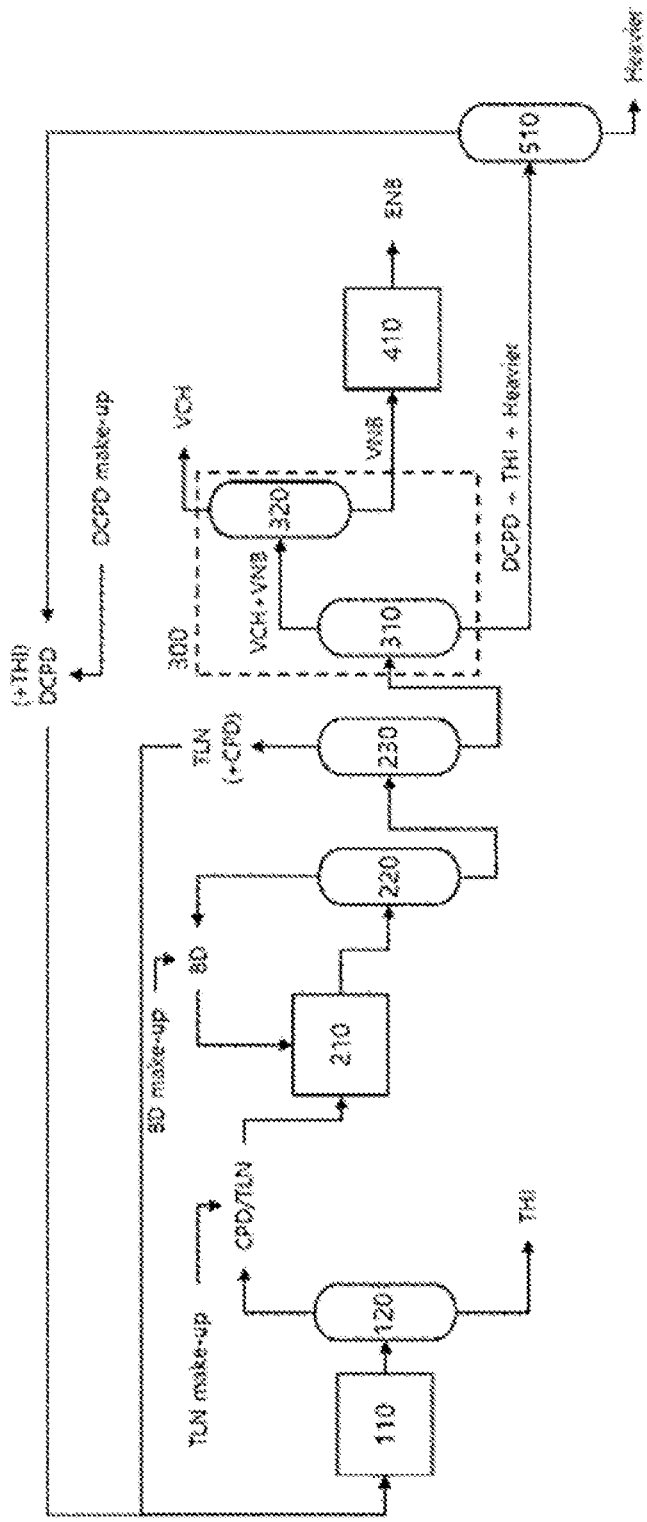
FIG. 1 shows a process flow chart illustrating one embodiment of the present specification.

Hereinafter, one aspect of the present specification will be described with reference to the accompanying drawings. However, the description of the present specification may be implemented in several different forms, and thus is not limited to the embodiments described herein. In order to clearly illustrate the present invention in the drawings, parts irrelevant to the description are omitted, and the same reference numerals are added to the same or similar parts throughout the specification.

Throughout the specification, when a part is "connected" to another part, this includes not only the case where it is "directly connected" but also the case where it is "indirectly connected" with another member interposed therebetween. In addition, when a part is said to "include" a component, this means that other components may be further included, not excluded, unless specifically stated otherwise.

When a range of numerical values is recited herein, the values have the precision of the significant figures provided in accordance with the standard rules in chemistry for significant figures, unless the specific range is otherwise stated. For example, 10 includes the range of 5.0 to 14.9, and the number 10.0 includes the range of 9.50 to 10.49.

Hereinafter, one embodiment of the present invention will be described in detail with reference to the accompanying drawings.

Preparation process of 5-ethylidene-2-norbornene

A preparation process of 5-ethylidene-2-norbornene according to one aspect of the present specification includes: step a-1 of introducing dicyclopentadiene (DCPD) into a DCPD decomposition reactor 110 to thermally decompose the DCPD; step a-2 of introducing a product of step a-1 into a cyclopentadiene (CPD) purification tower 120; step b-1 of introducing 1,3-butadiene (BD), a solvent, and cyclopentadiene separated from the top of the CPD purification tower 120 into a Diels-Alder reactor 210 to react the same; step b-2 of introducing a product of step b-1 into a BD removal tower 220 to recover 1,3-butadiene from the top; step b-3 of introducing a mixture at the bottom of the BD removal tower 220 into a desolvation tower 230, and recycling a solvent and unreacted raw materials recovered from the top of the desolvation tower 230 to the DCPD decomposition reactor 110; step c of introducing a mixture at a bottom of the desolvation tower 230 into a 5-vinyl-2-norbornene (VNB) separation tower 300 to separate 5-vinyl-2-norbornene; and step d of introducing the 5-vinyl-2-norbornene into an isomerization reactor 410 to react the same.

In step a-1, dicyclopentadiene is decomposed to prepare cyclopentadiene, and the DCPD decomposition reactor 110 may be a thermal decomposition reactor.

The dicyclopentadiene and the solvent and unreacted raw materials recovered from the top of the desolvation tower 230 may be introduced into the DCPD decomposition reactor 110. The unreacted raw material may include cyclopentadiene.

The dicyclopentadiene introduced into the DCPD decomposition reactor 110 may be dissolved in the solvent recovered from the top of the desolvation tower 230.

Dicyclopentadiene is a compound represented by the chemical formula $C_{10}H_{12}$ and may be converted into cyclopentadiene through a thermal decomposition reaction. Since the reaction is performed reversibly, the decomposed cyclopentadiene may be dimerized into dicyclopentadiene within a few hours at room temperature. Therefore, when using cyclopentadiene, efficient thermal decomposition of dicyclopentadiene is essential.

In a conventional 5-ethylidene-2-norbornene preparation process, a solvent recovered from a desolvation tower was recycled to a Diels-Alder reactor, and the solvent was not used in the dicyclopentadiene decomposition process. However, since dicyclopentadiene has a melting point of about 32.5° C. and is solid at room temperature, it is difficult to transfer when used alone, and there is a possibility of causing process troubles such as clogging of pumps and transfer pipes.

In the preparation process of 5-ethylidene-2-norbornene according to one aspect of the present specification, the solvent recovered from the top of the desolvation tower 230 is recycled to the DCPD decomposition reactor 110, so that dicyclopentadiene may be decomposed and transferred in a state of being dissolved in the solvent. When dicyclopentadiene is dissolved in a solvent, it is possible to prevent process troubles such as clogging of pumps and transfer pipes by maintaining a liquid phase, thereby improving the efficiency of the entire process.

As the solvent, a solvent capable of dissolving dicyclopentadiene and cyclopentadiene and not reacting with dicyclopentadiene or cyclopentadiene at a thermal decomposition temperature may be used.

The solvent may be a hydrocarbon solvent, and be, for example, at least one selected from the group consisting of propane, butane, pentane, hexane, octane, decane, dodecane, cyclopentane, methylcyclopentane, cyclohexane, benzene, toluene, xylene, dichloromethane, chloroethane, ethyl acetate, ethyl ether, ethanol, acetone, 1,2-dichloroethane, and chlorobenzene, but is not limited thereto.

The solvent may have a boiling point of 70 to 140° C. For example, the solvent may have a boiling point of 70° C., 75° C., 80° C., 85° C., 90° C., 95° C., 100° C., 105° C., 110° C., 115° C., 120° C., 125° C., 130° C., 135° C., 140° C., or in a range between two of these values. When the boiling point of the solvent is excessively low, the difference in boiling point between the solvent and cyclopentadiene or dicyclopentadiene is reduced, and thus purification efficiency may decrease.

Thermal decomposition of step a-1 may be performed at a temperature of 300 to 500° C. That is, the DCPD decomposition reactor 110 may include a thermal decomposition reaction portion adjusted to a temperature of 300 to 500° C. For example, the thermal decomposition of step a-1 may be performed at a temperature of 300° C., 310° C., 320° C., 330° C., 340° C., 350° C., 360° C., 370° C., 380° C., 390° C., 400° C., 410° C., 420° C., 430° C., 440° C., 450° C., 460° C., 470° C., 480° C., 490° C., 500° C., or in a range between two of these values. When the temperature of the thermal decomposition reaction is excessively low, the production of cyclopentadiene polymers may be suppressed to prevent clogging of the reactor, but thermal decomposition efficiency may decrease. When the temperature of the thermal decomposition reaction is excessively high, the cyclopentadiene polymer may be produced, resulting in a decrease in yield or clogging of the reactor.

Step a-1 may be performed as a continuous process, but is not limited thereto.

When step a-1 is performed as a continuous process, process efficiency may be improved. The thermal decomposition reaction of dicyclopentadiene is a reversible reaction, and cyclopentadiene dimerizes into dicyclopentadiene within several hours at room temperature, making it difficult to store for a long time. Therefore, when the thermal decomposition of dicyclopentadiene is performed in a batch process, cyclopentadiene is dimerized before being used in the next process, which may reduce process efficiency.

The DCPD decomposition reactor 110 is not limited on the type thereof such as a continuous tank reactor, a tubular reactor and the like, as long as the temperature and space velocity may be adjusted and a continuous process may be performed, but when the tubular reactor is used, it may be easy to maintain a uniform residence time and control the residence time.

Step a-1 may be a step of thermally decomposing dicyclopentadiene in the presence of an inert gas by introducing dicyclopentadiene into the DCPD decomposition reactor 110.

The dicyclopentadiene, the inert gas, and the solvent and unreacted raw materials recovered from the top of the desolvation tower 230 may be introduced into the DCPD decomposition reactor 110.

Step a-1 may be a step in which dicyclopentadiene, the inert gas, and the solvent and unreacted raw materials recovered from the top of the desolvation tower 230 are introduced into the DCPD decomposition reactor 110, and a dicyclopentadiene solution dissolved in the solvent is thermally decomposed in the presence of the inert gas.

When the thermal decomposition reaction is continuously performed with only the dicyclopentadiene solution for a long time, a cyclopentadiene polymer may be produced in the reactor, resulting in a decrease in yield or clogging of the reactor. This reactor blockage may be prevented by introducing the inert gas into the reactor at the same time. The inert gas reduces the residence time of the reactant in the zone where clogging of the reactor occurs, thereby suppressing the reduction in decomposition efficiency and preventing clogging.

The inert gas may be transferred together with the dicyclopentadiene or the solvent, or may be transferred separately and mixed inside the DCPD decomposition reactor 110. When the dicyclopentadiene, solvent, and inert gas are transferred together at an inlet of the DCPD decomposition reactor 110, the reactant residence time at the inlet of the reactor where clogging of the reactor most frequently occurs is reduced, thereby improving efficiency.

The inert gas may be a gas that is not reactive at the thermal decomposition reaction temperature of dicyclopentadiene. For example, the inert gas may be at least one selected from the group consisting of nitrogen, argon, neon, and helium, but is not limited thereto.

When the residence time of the reactants in the DCPD decomposition reactor 110 is long, a cyclopentadiene polymer may be prepared and the yield may decrease, or the reactor may be clogged, and when the residence time of the reactants is short, thermal decomposition efficiency may decrease, but when the thermal decomposition reaction is performed in the presence of an inert gas, thermal decomposition efficiency may be improved while suppressing clogging of the reactor by addressing this trade-off relationship.

Step a-2 is a step of introducing a product of step a-1 into the CPD purification tower 120 to purify cyclopentadiene, and at the top of the CPD purification tower 120, high-purity cyclopentadiene may be isolated.

The number of stages of the CPD purification tower 120 may be 30, a reflux ratio may be 5.3, and the number of feed stages may be 15, but is not limited thereto.

Step b-1 is a step of preparing 5-vinyl-2-norbornene by a Diels-Alder reaction between cyclopentadiene and 1,3-butadiene.

In step b-1, a polymerization inhibitor may be further introduced into the Diels-Alder reactor 210. The polymerization inhibitor may prevent 5-vinyl-2-norbornene, which is a product of the Diels-Alder reaction, from reacting with oxygen or moisture in the air to form an oxide.

In addition to 5-vinyl-2-norbornene, a product of the step b-1 may include unreacted cyclopentadiene, unreacted 1,3- butadiene, a solvent, and by-products of the Diels-Alder reaction such as 4-vinyl-cyclohexene (VCH), dicyclopentadiene, 3a,4,7,7a-tetrahydroindene (THI), and other high-boiling point compounds (Heavier). The unreacted raw materials, the by-products, or the polymerization inhibitor included in the product of the step b-1 may act as catalyst inactivation factors during a subsequent isomerization reaction of 5-vinyl-2-norbornene, and thus are preferably removed.

In step b-1, a molar ratio of cyclopentadiene and 1,3-butadiene introduced into the Diels-Alder reactor 210 may range from 1:2 to 1:4. For example, the molar ratio may be 1:2, 1:2.5, 1:3, 1:3.5, 1:4, or in a range between two of these molar ratios. When a molar ratio of 1,3-butadiene to cyclopentadiene introduced into the Diels-Alder reactor 210 is less than the above range, an amount of 5-vinyl-2-norbornene produced may decrease, and when the molar ratio exceeds the above range, an amount of 4-vinyl-cyclohexene produced as a by-product may increase.

Step b-2 is a step in which a product of step b-1 is introduced into a BD removal tower 220 to recover 1,3-butadiene.

In the Diels-Alder reaction, a conversion rate of 1,3-butadiene is 10% or less, and 1,3-butadiene may occupy the highest proportion among materials discharged from the rear end of the Diels-Alder reactor 210. Therefore, by first separating 1,3-butadiene, it is possible to reduce the size and operating costs of a device in a subsequent process.

1,3-Butadiene recovered from the top of the BD removal tower 220 may be recycled to the Diels-Alder reactor 210. 1,3-Butadiene may be recovered with high-purity and reused in the Diels-Alder reaction due to having a low boiling point.

The number of stages of the BD removal tower 220 may be 20, a reflux ratio may be 0.8, and the number of feed stages may be 13, but is not limited thereto.

Step b-3 is a step in which a mixture at the bottom of the BD removal tower 220 is introduced into a desolvation tower 230 to recycle a solvent and an unreacted raw material, which is cyclopentadiene, recovered from the top of the desolvation tower 230 to the DCPD decomposition reactor 110.

As described above, the solvent recovered in step b-3 and recycled to the DCPD decomposition reactor 110 is capable of dissolving dicyclopentadiene, and by decomposing and transferring dicyclopentadiene in a solution state, it is possible to prevent process troubles such as clogging of pumps and transfer pipes, and to improve the decomposition stability of dicyclopentadiene. In addition, step b-3 may improve the efficiency of the entire process by minimizing raw material loss by recycling the recovered unreacted raw materials together.

In the Diels-Alder reaction, a conversion rate of cyclopentadiene is 88% or more, and an amount of residual cyclopentadiene is small, so that it may be advantageous to separate it with a solvent.

The number of stages of the desolvation tower 230 may be 60, a reflux ratio may be 2.4, and the number of feed stages may be 22, but is not limited thereto.

Step c is a step in which the mixture at the bottom of the desolvation tower 230 is introduced into the 5-vinyl-2-norbornene separation tower 300 to separate and purify 5-vinyl-2-norbornene.

The VNB separation tower 300 includes a first VNB separation tower 310 and a second VNB separation tower 320, and step c may include step c-1 introducing the mixture at the bottom of the desolvation tower 230 into the first VNB separation tower 310 to introduce a mixture separated from the top of the first VNB separation tower 310 into the second VNB separation tower 320, and step c-2 separating 5-vinyl-2-norbornene from the bottom of the second VNB separation tower 320.

Step c-1 is a step in which the mixture at the bottom of the desolvation tower 230 is introduced into the first VNB separation tower 310 to introduce a mixture separated from the top of the first VNB separation tower 310 into the second VNB separation tower 320.

The mixture separated from the top of the first VNB separation tower 310 may include 5-vinyl-2-norbornene and 4-vinyl-cyclohexene (VCH).

In the conventional 5-ethylidene-2-norbornene preparation process, 4-vinyl-cyclohexene, 5-vinyl-2-norbornene, and dicyclopentadiene were sequentially separated in order of boiling point, but in this case, there is a problem in that utility usage increases. In addition, boiling points of 4-vinyl-cyclohexene and 5-vinyl-2-norbornene are 128.9° C. and 141° C., respectively, and when 4-vinyl-cyclohexene is separated alone, the loss of 5-vinyl-2-norbornene may increase because the difference in boiling point from that of 5-vinyl-2-norbornene is not large. In order to separate high-purity 5-vinyl-2-norbornene, a column having a high number of stages and a high reflux ratio is required.

In the preparation process of 5-ethylidene-2-norbornene according to one aspect of the present specification, 4-vinyl-cyclohexene and 5-vinyl-2-norbornene are first separated at the same time, and thus it is economical because it may reduce utility usage and facility size. In addition, high purity 5-vinyl-2-norbornene may be obtained by separating 5-vinyl-2-norbornene from a mixture of 4-vinyl-cyclohexene and 5-vinyl-2-norbornene using a separate column and raw material loss may be minimized.

The number of stages of the first VNB separation tower 310 may be 40, a reflux ratio may be 2.7, and the number of feed stages may be 21, but is not limited thereto.

Step c-2 is a step of separating 5-vinyl-2-norbornene from the bottom of the second VNB separation tower 320.

Since the 5-vinyl-2-norbornene separated in step c-2 has high purity, it is possible to prevent catalyst inactivation in a subsequent isomerization reaction.

4-Vinyl-cyclohexene may be separated from the top of the second VNB separation tower 320.

The number of stages of the second VNB separation tower 320 may be 70, a reflux ratio may be 16.8, and the number of feed stages may be 30, but is not limited thereto.

Step d is a step of preparing 5-ethylidene-2-norbornene by an isomerization reaction of 5-vinyl-2-norbornene.

In step d, the purity of the 5-vinyl-2-norbornene introduced into the isomerization reactor 410 may be 99% or more. For example, the purity may be 99.0 wt %, 99.1 wt %, 99.2 wt %, 99.3 wt %, 99.4 wt %, 99.5 wt %, 99.6 wt %, 99.7 wt %, 99.8 wt %, 99.9 wt % or more.

Step d may include step d-1 of filling the isomerization reactor 410 with a catalyst; and step d-2 of introducing the 5-vinyl-2-norbornene into the isomerization reactor 410 to react it.

Step d-1 is a step of filling the isomerization reactor 410 with a catalyst, and as the isomerization reactor 410, a batch reactor, a semi-batch reactor, a continuous mixing reactor, a tubular reactor, a continuous fixed bed reactor, and the like may be used. Since the catalyst may be in a solid state and 5-vinyl-2-norbornene is in a liquid state at room temperature, a reactor may be selected according to these characteristics. For example, a tubular reactor may be selected as the isomerization reactor 410. A reactant inlet is provided at one end of the tubular reactor and a product outlet is provided at the other end, and the catalyst may be filled in all or part of a spatial area of the tubular reactor.

In step d-1, an adsorbent may be further input into the isomerization reactor 410. The adsorbent may be positioned before the catalyst according to the flow direction of the raw material. An inactivation component of the catalyst may be removed through the adsorbent. Typical adsorbents in the art may be used. For example, examples of the adsorbent include, but are not limited to, alumina, silica alumina, molecular sieve 3A, and zeolite.

Step d-2 is a step of reacting by introducing 5-vinyl-2-norbornene as a raw material into the isomerization reactor 410 filled with a catalyst.

A temperature of the isomerization reactor 410 in step d-2 may be maintained at 10 to 50° C. For example, the temperature may be 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or in a range between two of these values. In a reaction of converting 5-vinyl-2-norbornene to 5-ethylidene-2-norbornene, when a reaction temperature is high, the conversion rate may be high, but production of by-products may also increase, and conversely, when the reaction temperature is low, high selectivity may be exhibited, but in addition to a low conversion rate, catalyst inactivation due to adsorption of by-products may be caused. Under conditions satisfying the above range, an inactivation factor is minimized and the reaction may be stably performed.

A reaction of step d-2 may be performed while satisfying conditions of atmospheric pressure, for example, 0.5 to 1.5 bar, but is not limited thereto.

In step d-2, a space velocity of 5-vinyl-2-norbornene as a raw material may be 5.0/h or less. For example, the space velocity of the raw material may be 5.0/h, 4.9/h, 4.8/h, 4.7/h, 4.6/h, 4.5/h, 4.4/h, 4.3/h, 4.2/h, 4.1/h, 4.0/h, 3.9/h, 3.8/h, 3.7/h, 3.6/h, 3.5/h, 3.4/h, 3.3/h, 3.2/h, 3.1/h, 3.0/h, 2.9/h, 2.8/h, 2.7/h, 2.6/h, 2.5/h, 2.4/h, 2.3/h, 2.2/h, 2.1/h, 2.0/h, 1.9/h, 1.8/h, 1.7/h, 1.6/h, 1.5/h, 1.4/h, 1.3/h, 1.2/h, 1.1/h, 1.0/h, 0.9/h, 0.8/h, 0.7/h, 0.6/h, 0.5/h, 0.4/h, 0.3/h, 0.2/h, 0.1/h. However, when 5-ethylidene-2-norbornene produced in the reactor stays in a catalyst layer at a stagnant level, there is room for oligomers to be prepared by polymerization of 5-ethylidene-2-norbornene. Accordingly, it is necessary to manage flowability at a certain level or higher, and for example, the space velocity of 5-ethylidene-2-norbornene may be 0.05/h or more. The reaction of converting 5-vinyl-2-norbornene to 5-ethylidene-2-norbornene is an exothermic reaction, and since heat generated as the reaction proceeds is used to increase a reaction temperature, a reaction rate is excessively increased. Accordingly, the degree of heat generation per unit area of the reactor may be controlled by adjusting the space velocity of the raw material, and the inactivation factor is minimized under conditions satisfying the above range, so that a reaction between the catalyst and the raw material may be stably performed. Here, the space velocity of the raw material means the reciprocal of the time required for 5-vinyl-2-norbornene to pass through the catalyst filled in the reactor, and when an apparent volume of the catalyst is $V_p$ (ml) and the feed rate of the raw material is V (ml/h), the space velocity of the raw material is defined as $V/V_p$.

In step d-2, a linear velocity of 5-vinyl-2-norbornene as a raw material may be 0.01 to 2 cm/min. For example, the linear velocity may be 0.01 cm/min, 0.02 cm/min, 0.03 cm/min, 0.04 cm/min, 0.05 cm/min, 0.06 cm/min, 0.07 cm/min, 0.08 cm/min, 0.09 cm/min, 0.1 cm/min, 0.2 cm/min, 0.3 cm/min, 0.4 cm/min, 0.5 cm/min, 0.6 cm/min, 0.7 cm/min, 0.8 cm/min, 0.9 cm/min, 1 cm/min, 1.1 cm/min, 1.2 cm/min, 1.3 cm/min, 1.4 cm/min, 1.5 cm/min, 1.6 cm/min, 1.7 cm/min, 1.8 cm/min, 1.9 cm/min, 2 cm/min, or in a range between two of these values. Under conditions satisfying the above range, catalytic activity and stability may be controlled by controlling the movement velocity of the raw material. Here, the linear velocity of the raw material means the movement velocity of the raw material when 5-vinyl-2-norbornene passes through the catalyst filled in the reactor, and when the feed rate of the raw material is V (ml/h) and the cross-sectional area of the reactor is S ($cm^2$), the linear velocity is defined as V/S.

In step d-2, an adsorbent may be further input into the isomerization reactor 410, or the raw material passing through the adsorbent may be used. When the adsorbent is input, it may be positioned before the catalyst according to the flow direction of the raw material. An inactivation component of the catalyst may be removed through the adsorbent. Examples of the adsorbent include, but are not limited to, alumina, silica, molecular sieves 3A, and zeolite.

Step d-2 may be performed in a batch or continuous mode. The isomerization reactor 410 may be selected according to the type described above.

In step d-2, a diameter of the isomerization reactor 410 may be 0.25 to 1.5 inches. For example, the diameter may be 0.25 inches, 0.26 inches, 0.27 inches, 0.28 inches, 0.29 inches, 0.3 inches, 0.4 inches, 0.5 inches, 0.6 inches, 0.7 inches, 0.8 inches, 0.9 inches, 1 inch, 1.2 inches, 1.3 inches, 1.4 inches, 1.5 inches, or in a range between two of these values, but is not limited thereto. The diameter of the reactor may be 1.5 inches or more while adjusting the space velocity and linear velocity of the raw material as necessary. When the diameter of the reactor is too small, it may be difficult to maintain proper productivity, and conversely, when the diameter of the reactor is too large, it is difficult to control heat generation and the inactivity of the catalyst may rapidly progress.

The conversion rate in step d-2 may be maintained at 98.5% or more. 5-Vinyl-2-norbornene, which is a reactant, and 5-ethylidene-2-norbornene, which is a product, have similar boiling points of 140° C. and 146° C., respectively, making it difficult to separate and purify. Therefore, it is advantageous to convert 98.5% or more and use it as a raw material for EPDM directly without separation and purification, and when the conversion rate is too low, it is preferable to increase the conversion rate to 98.5% or more by passing the product through a catalyst layer again.

Steps d-1 to d-2 may be performed at an oxygen concentration of 100 ppm or less, for example, 100 ppm, 95 ppm, 90 ppm, 85 ppm, 80 ppm, 75 ppm, 70 ppm, 65 ppm, 60 ppm, 55 ppm, 50 ppm, 45 ppm, 40 ppm, 35 ppm, 30 ppm, 25 ppm, 20 ppm, 15 ppm, 10 ppm, 5 ppm or less. Inactivation factors of the catalyst may be suppressed by controlling the oxygen concentration within the above range in the reactor.

The catalyst may be a base catalyst. For example, the catalyst may be a catalyst in which an alkali metal or alkaline earth metal is supported on a surface of a basic support.

The catalyst is a catalyst for preparing 5-ethylidene-2-norbornene and may mediate an isomerization reaction of 5-vinyl-2-norbornene. Generally, the catalyst may be prepared by mixing active ingredients such as a main catalyst, a promoter, a co-catalyst, a support, and the like. A catalyst in which an active ingredient is supported on the support is called a supported catalyst.

In order to prepare high-purity 5-ethylidene-2-norbornene, a catalyst with stability and excellent performance is required. When a catalyst with insufficient performance is used, the conversion rate of 5-vinyl-2-norbornene is low, so that the cost of separation and purification increases, and an amount of recycled raw material increases, resulting in an increase in size of the device. When a catalyst with insufficient stability is used, it is necessary to periodically replace the catalyst, which increases catalyst costs and reduces economic feasibility due to process stoppage.

Conventionally, an alkali metal hydroxide or alkaline earth metal hydroxide has been combined with the alkali metal or alkaline earth metal to prepare a highly active and stable catalyst, but the preparation process is complicated and a sufficient level of stability is not provided.

The catalyst may be a solid catalyst prepared by a method including: step 1 of heat-treating the basic support; step 2 of mixing the heat-treated basic support with the alkali metal or alkaline earth metal to obtain a mixture; and step 3 of heat-treating the mixture.

The catalyst prepared using a basic support may have excellent activity and stability at the same time. When the catalyst is used, 5-ethylidene-2-norbornene may be prepared while maintaining a high conversion rate for a long time, and thus high-purity 5-ethylidene-2-norbornene may be prepared. The catalyst according to the above-mentioned preparation method may be applied in both batch and continuous modes.

The basic support may satisfy at least one of the following conditions (i) to (iii), but is not limited thereto.

(i) A pH may be 8.5 to 11, for example 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3; 10.4, 10.5, 10.6, 10.7, 10.8, 10.9, 11.0 or in a range between two of these values. When the pH satisfies the above range, catalyst stability may be better.

(ii) An average particle diameter may be 30 to 500 μm, for example, 30 μm, 35 μm, 40 μm, 45 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 310 μm, 320 μm, 330 μm, 340 μm, 350 μm, 360 μm, 370 μm, 380 μm, 390 μm, 400 μm, 410 μm, 420 μm, 430 μm, 440 μm, 450 μm, 460 μm, 470 μm, 480 μm, 490 μm, 500 μm, or in a range between two of these values. When the average particle diameter satisfies the above range, the prepared catalyst may be more suitable for a continuous fixed bed reactor.

(iii) A BET specific surface area may be 150 to 250 $m^2/g$, for example, 150 $m^2/g$, 155 $m^2/g$, 160 $m^2/g$, 165 $m^2/g$, 170 $m^2/g$, 175 $m^2/g$, 180 $m^2/g$, 185 $m^2/g$, 190 $m^2/g$, 195 $m^2/g$, 200 $m^2/g$, 205 $m^2/g$, 210 $m^2/g$, 215 $m^2/g$, 220 $m^2/g$, 225 $m^2/g$, 230 $m^2/g$, 235 $m^2/g$, 240 $m^2/g$, 245 $m^2/g$, 250 $m^2/g$, or in a range between two of these values. When the specific surface area satisfies the above range, the activity of the catalyst may be more excellent.

An example of the basic support that satisfies these conditions is basic alumina, but is not limited thereto.

A catalyst using the basic support may have significantly better activity or stability than a catalyst prepared by treating an acidic or neutral support with a base to adjust basicity.

Step 1 may be a step of heat-treating the basic support to remove a component that lowers the activity of the catalyst. Since the basic support has a large surface area and developed pores, it adsorbs moisture and oxygen in air during storage. When step 1 is not performed, loss of active ingredients may occur during a catalyst preparation process, and it may be difficult to prepare a catalyst having uniform performance.

The heat treatment of step 1 may be performed at a temperature of 150 to 500° C., for example, 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., 350° C., 360° C., 370° C., 380° C., 390° C., 400° C., 410° C., 420° C., 430° C., 440° C., 450° C., 460° C., 470° C., 480° C., 490° C., 500° C., or in a range between two of these values. When the heat treatment temperature satisfies the above range, it is possible to suppress denaturation of the basic support and sufficiently remove components to be removed. When the temperature of the step 1 is too low, removal of the component to be removed is not sufficient, or when the temperature is too high for heat treatment, there is a risk that the support may deteriorate, such as causing phase transition or changing pore characteristics.

The heat treatment of step 1 may be performed for 0.5 to 10 hours, for example, 0.5 hours, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, or for a time in a range between two of these values. When the heat treatment time satisfies the above range, it is possible to suppress denaturation of the basic support and sufficiently remove components to be removed.

The heat treatment of step 1 may be performed under an inert gas atmosphere such as Ar, $N_2$, or He, preferably under an Ar atmosphere. Ar is heavier than air and may effectively block contact with air.

In step 1, the basic support may be stirred to increase uniformity and shorten the heat treatment time, and in this case, a stirring speed may be appropriately adjusted within a range in which the basic support is evenly mixed and not scattered.

Step 2 may be a step of supporting the alkali metal or alkaline earth metal to be a catalyst component on a basic support. The alkali metal used as the catalyst component may be one of lithium, sodium, potassium, rubidium, cesium, and francium, and the alkaline earth metal may be one of beryllium, magnesium, calcium, strontium, barium, and radium. As the catalyst component, one or more alkali metals, one or more alkaline earth metals, or a mixture of one or more alkali metals and one or more alkaline earth metals may be used.

Step 2 may be performed at a temperature of Tm+20 to 80° C., for example, Tm+20° C., Tm+25° C., Tm+30° C., Tm+35° C., Tm+40° C., Tm+45° C., Tm+50° C., Tm+55° C., Tm+60° C., Tm+65° C., Tm+70° C., Tm+75° C., Tm+80° C., or in a range between two of these values. When this temperature range is satisfied, the catalyst component may be more easily supported on the support. When the temperature of step 2 is too low, the catalyst component may not penetrate into the basic support or it may take an excessively long time. Conversely, when the temperature is too high, it is difficult to ensure uniformity because the catalyst component partially and rapidly penetrates the support, and in the case of some metals, for example, Na, hydrogen gas may be generated in a process of mixing with the basic support, and rapid release of hydrogen at such a high temperature may cause stability problems by increasing the pressure inside a catalyst preparation reactor. Here, Tm means a melting point of an alkali metal or alkaline earth metal serving as a catalyst component, and in the case of using two or more alkali metals or alkaline earth metals, means a melting point of the alkali metal or alkaline earth metal having the highest melting point.

Step 2 may be performed for a time of 0.5 to 10 hours, for example, 0.5 hours, 1 hour, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, or for a time in a range between two of these values. When the time of the step 2 satisfies the above range, the catalyst component may be more easily supported on the support.

A weight of the alkali metal or alkaline earth metal relative to a volume of the basic support may be 0.05 to 0.5 g/mL, for example, 0.05 g/mL, 0.06 g/mL, 0.07 g/mL, 0.08 g/mL, 0.09 g/mL, 0.1 g/mL, 0.11 g/mL, 0.12 g/mL, 0.13 g/mL, 0.14 g/mL, 0.15 g/mL, 0.16 g/mL, 0.17 g/mL, 0.18 g/mL, 0.19 g/mL, 0.2 g/mL, 0.21 g/mL, 0.22 g/mL, 0.23 g/mL, 0.24 g/mL, 0.25 g/mL, 0.26 g/mL, 0.27 g/mL, 0.28 g/mL, 0.29 g/mL, 0.3 g/mL, 0.35 g/mL, 0.4 g/mL, 0.45 g/mL, 0.5 g/mL, or in a range between two of these values. When the above range is satisfied, a catalyst having excellent catalytic activity and excellent stability may be prepared.

In step 2, the catalyst component may be stirred so that it may be easily supported on the basic support, and in this case, the stirring speed may be properly adjusted within the range of maintaining uniform reaction conditions while preventing aggregation of the catalyst component and the basic support.

Step 3 may be a step of optimizing the bond between the support and the active material by heat-treating the catalyst in which the active material is supported on the support.

The heat treatment of step 3 may be performed at a temperature of Tm+50° C., Tm+55° C., Tm+60° C., Tm+65° C., Tm+70° C., Tm+75° C., Tm+80° C., Tm+85° C., Tm+90° C., Tm+95° C., Tm+100° C., Tm+105° C., Tm+110° C., Tm+115° C., Tm+120° C., Tm+125° C., Tm+130° C., Tm+135° C., Tm+140° C., Tm+145° C., Tm+150° C., or in a range between two of these values. More specifically, the heat treatment may be performed at Tm+85° C. to Tm+145° C., and may be performed at Tm+90° C. to Tm+140° C. When the heat treatment is performed within a range satisfying the above range, catalytic activity and stability may be simultaneously improved. When the temperature of step 3 is too low, it may be difficult to expect stable catalytic activity because the bond between the basic support and the catalyst component is weak, and conversely, when the temperature of step 3 is too high, there is a risk that the catalyst component penetrates deeply into pores of the support and rather lowers the activity.

The heat treatment of step 3 may be performed for a time of 0.5 to 5 hours, for example, 0.5 hours, 1 hour, 1.5 hours, 2 hours, 2.5 hours, 3 hours, 3.5 hours, 4 hours, 4.5 hours, 5 hours, or for a time in a range between two of these values. When the above range is satisfied, unnecessary waste of time may be minimized and catalytic stability may be improved.

Steps 1 to 3 may be performed at an oxygen concentration of 100 ppm or less, for example, 100 ppm, 95 ppm, 90 ppm, 85 ppm, 80 ppm, 75 ppm, 70 ppm, 65 ppm, 60 ppm, 55 ppm, 50 ppm, 45 ppm, 40 ppm, 35 ppm, 30 ppm, 25 ppm, 20 ppm, 15 ppm, 10 ppm, 5 ppm or less. Measurement of the oxygen concentration may be performed using a method commonly used in the art, for example, a diaphragm electrode type, a magnetic type or zirconia type oximeter. This oxygen concentration may be achieved by substituting the reactor with an inert gas such as nitrogen, argon, helium, and the like. As the inert gas substitution method, any method such as vacuum substitution, pressure substitution, sweep substitution, siphon substitution, or the like may be used as long as the oxygen concentration described above may be achieved.

After step 3, the reactor used for preparing the catalyst is cooled to room temperature, and then the isomerization reactor 410 may be directly charged with the catalyst. Oxygen, moisture, by-products, and the like which may act as inactivation factors of the catalyst, are removed from the raw material stage, and the prepared catalyst is filled in the isomerization reactor 410 while maintaining an inert gas atmosphere to maximize catalytic activity and stability.

The method of preparing the catalyst may prepare a catalyst having excellent activity and stability by a simple method without post-treatment such as a separate additional molding process.

The catalyst may be a solid catalyst, but is not limited thereto.

The catalyst may be a solid catalyst slurry prepared by a method further including step 4 of inputting the solid catalyst into at least one solvent selected from the group consisting of heptane, toluene, and paraffin oil.

The solid catalyst slurry may be charged into the isomerization reactor 410.

When the solid catalyst is exposed to air, oxidation occurs and activity is lowered, and when exposed to moisture, there is a risk of explosion due to the generation of hydrogen at the same time as the exothermic reaction. In particular, the solid catalyst in the form of powder has a high surface area and high dispersion of the active material, so that the risk may be further increased.

At least one solvent selected from the group consisting of heptane, toluene, and paraffin oil may have low reactivity because it does not contain an oxygen atom, and may be non-volatile at room temperature due to its low vapor pressure.

The solid catalyst slurry is blocked from contact with poisonous substances by a solvent, and may be safely stored, transferred, and filled in a reactor in a slurry state, not in a solid state, so that catalytic activity may be stably excellent.

The solid catalyst slurry may be prepared by inputting the solid catalyst into at least one solvent selected from the group consisting of heptane, toluene, and paraffin oil in an inert gas atmosphere.

Step d may further include step d-3 of inputting a spent catalyst used in the reaction into at least one solvent selected from the group consisting of heptane, toluene, and paraffin oil to obtain a spent catalyst slurry; and step d-4 of inputting water to the spent catalyst slurry to oxidize the catalyst.

In step d-3, by preparing a spent catalyst in the form of a slurry, it is possible to minimize the risk by preventing a reaction of the residual active material and blocking contact with air and moisture. For example, after completion of the reaction, reactants and products and the spent catalyst may be separated through a nitrogen purge, and a solvent may be input into the spent catalyst to prepare the spent catalyst slurry. The prepared spent catalyst slurry may be stably transferred to a separate reactor.

In step d-4, the catalyst may be oxidized by inputting water while stirring the spent catalyst slurry transferred to a separate reactor, and water may be input while gradually adjusting so that excessive heat is not generated.

A volume ratio of the spent catalyst and water may be 1:0.1 to 0.4. For example, the volume ratio may be 1:0.1, 1:0.15, 1:0.2, 1:0.25, 1:0.3, 1:0.35, 1:0.4, or in a range between two of these values. The spent catalyst completely oxidized by water may be separated after precipitating to the bottom of the solvent and the used solvent and the solvent containing water may be layer-separated and reused. The spent catalyst completely oxidized in step d-4 may be safely discarded by removing residual active materials.

A preparation process of 5-ethylidene-2-norbornene according to one aspect of the present specification may further include step e of introducing a mixture at the bottom of the first VNB separation tower 310 into a DCPD recovery tower 510 to recycle materials recovered from the top of the DCPD recovery tower 510 to the DCPD decomposition reactor 110.

Step e is a step of separating a mixture including the dicyclopentadiene fraction from the bottom of the first VNB separation tower 310, introducing the mixture into the DCPD recovery tower 510, and recycling materials recovered from the top of the DCPD recovery tower 510 to the DCPD decomposition reactor (110).

The materials recovered from the top of the DCPD recovery tower 510 may include dicyclopentadiene and 3a,4,7,7a-tetrahydroindene (THI) produced as by-products of the Diels-Alder reaction.

Since dicyclopentadiene among the materials recovered from the top of the DCPD recovery tower 510 may be converted into cyclopentadiene through a decomposition reaction, loss of raw materials may be minimized by recovering and recycling the dicyclopentadiene.

The 3a,4,7,7a-tetrahydroindene may be separated from the bottom of the CPD purification tower 120.

In the DCPD decomposition reactor 110, since 3a,4,7,7a-tetrahydroindene remains undecomposed, and dicyclopentadiene is decomposed into cyclopentadiene, in the CPD purification tower 120, high-purity cyclopentadiene may be recovered by separating 3a,4,7,7a-tetrahydroindene.

In a conventional 5-ethylidene-2-norbornene preparation process, 3a,4,7,7a-tetrahydroindene is separated from a mixture of dicyclopentadiene and 3a,4,7,7a-tetrahydroindene recovered after the Diels-Alder reaction, but in this case, dicyclopentadiene may be decomposed during a separation process to produce cyclopentadiene, and cyclopentadiene may be separated along with 3a,4,7,7a-tetrahydroindene, resulting in an increase in raw material loss.

In a preparation process of 5-ethylidene-2-norbornene according to one aspect of the present specification, 3a,4,7, 7a-tetrahydroindene is recycled together with dicyclopentadiene to the DCPD decomposition reactor 110, and then 3a,4,7,7a-tetrahydroindene is separated in the CPD purification tower 120, so that the recovery rate of cyclopentadiene may be increased to minimize raw material loss. In addition, since dicyclopentadiene and 3a,4,7,7a-tetrahydroindene have a boiling point of 170° C. and 160° C., respectively, and the difference is not large, it may be advantageous to recover them together.

Step e may further include separating a high boiling point compound from the bottom of the DCPD recovery tower 510. Since a compound having a high boiling point may cause problems in operation of a subsequent reactor or pump, it is preferable to remove the compound.

The number of stages of the DCPD recovery tower 510 may be 10, a reflux ratio may be 0.5, and the number of feed stages may be 7, but is not limited thereto.

Hereinafter, examples of the present specification will be described in more detail. However, the following experimental results describe only representative experimental results among the examples, and the scope and content of the present invention may not be construed as reduced or limited by the examples. Each effect of the various embodiments of the present invention not explicitly presented below will be specifically described in the corresponding section.

EXAMPLES

An embodiment of the present specification provides a preparation process of 5-ethylidene-2-norbornene, and will be described with reference to FIG. 1.

Dicyclopentadiene (DCPD) is introduced into a DCPD decomposition reactor 110 for thermal decomposition, and a product is introduced into a cyclopentadiene (CPD) purification tower 120. CPD is separated from the top of the CPD purification tower 120, and 3a,4,7,7a-tetrahydroindene (THI) is separated from the bottom.

1,3-Butadiene (BD), toluene (TLN), and CPD separated from the top of the CPD purification tower 120 are introduced into a Diels-Alder reactor 210 to react them, and a product is introduced into a BD removal tower 220. BD is recovered from the top of the BD removal tower 220 and recycled to the Diels-Alder reactor 210, and a mixture at the bottom of the BD removal tower is introduced into a desolvation tower 230. TLN and unreacted CPD recovered from the top of the desolvation tower 230 are recycled to the DCPD decomposition reactor 110, and a mixture at the bottom is introduced into a first 5-vinyl-2-norbornene (VNB) separation tower 310.

The mixture separated from the top of the first VNB separation tower 310 is introduced into a second VNB separation tower 320, and the mixture at the bottom is introduced into a DCPD recovery tower 510. 4-Vinylcyclohexene (VCH) is separated from the top of the second VNB separation tower 320, and VNB is separated from the bottom, introduced into an isomerization reactor 410, and then reacted.

In the isomerization reactor 410, 5-ethylidene-2-norbornene (ENB) is obtained.

Materials recovered from the top of the DCPD recovery tower 510 are recycled to the DCPD decomposition reactor 110, and high boiling point compounds (Heavier) are separated from the bottom.

Experimental Example 1: DCPD Decomposition Reactor

A reaction in a DCPD decomposition reactor 110 according to reaction conditions was evaluated.

Experimental Example 1-1

A reaction mixture in which 77 parts by mole of dicyclopentadiene was dissolved in 21 parts by mole of toluene was continuously input into an upper part of a reactor at a temperature of 350° C. through a pump. 2 parts by mole of nitrogen was continuously input into the reactor. In the reactor, 99 mol % of dicyclopentadiene was thermally decomposed into cyclopentadiene, and clogging did not occur.

Experimental Example 1-2

A thermal decomposition reaction of dicyclopentadiene was performed in the same manner as in Experimental Example 1-1, except that a reaction mixture in which 72 parts by mole of dicyclopentadiene was dissolved in 20 parts by mole of toluene was used and an amount of nitrogen input into the reactor was increased to 9 parts by mole. 99 mol % of dicyclopentadiene was thermally decomposed into cyclopentadiene, and clogging did not occur.

Experimental Example 1-3

A thermal decomposition reaction of dicyclopentadiene was performed in the same manner as in Experimental Example 1-1, except that a reaction mixture in which 66 parts by mole of dicyclopentadiene was dissolved in 18 parts by mole of toluene was used, and the amount of nitrogen input into the reactor was increased to 16 parts by mole. 94 mol % of dicyclopentadiene was thermally decomposed into cyclopentadiene, and clogging did not occur.

Experimental Example 1-4

A thermal decomposition reaction of dicyclopentadiene was performed in the same manner as in Experimental Example 1-1, except that a reaction mixture in which 80 parts by mole of dicyclopentadiene was dissolved in 20 parts by mole of toluene was used, and nitrogen was not input into the reactor. In the reactor, 99 mol % of dicyclopentadiene was initially thermally decomposed into cyclopentadiene, but after a certain period of time, the internal pressure increased and clogging occurred at an inlet of the reactor after about 48 hours.

Experimental Example 1-5

A thermal decomposition reaction of dicyclopentadiene was performed in the same manner as in Experimental Example 1-4, except that a reaction mixture in which 50 parts by mole of dicyclopentadiene was dissolved in 50 parts by mole of toluene was used, but clogging occurred in the same way, except that the time point of clogging was delayed to after about 70 hours.

Experimental Example 1-6

A reaction was performed in the same manner as in Experimental Example 1-4, except that a thermal decomposition reaction of dicyclopentadiene was performed in a reactor at 300° C. Clogging did not occur, but a thermal decomposition rate fell to 91 mol %.

Comparative Experimental Example 1-1

Dicyclopentadiene was in a solid state similar to a candle at room temperature, so that it was impossible to transfer it using a pump.

Comparative Experimental Example 1-2

Dicyclopentadiene and nitrogen were mixed at a molar ratio of 98:2, but transfer using a pump was impossible due to dicyclopentadiene being a solid at room temperature.

Preparation Example 1: Isomerization Catalyst

Neutral alumina powder, basic alumina powder, or neutral alumina balls were prepared. After the alumina powder or balls were input into the reactor, the temperature was raised to 350° C. Thereafter, the inside was substituted with argon which is an inert gas, and maintained for 2 hours, and then the reactor was cooled to 150° C. Sodium metal was input to be 0.12 g/mL based on an alumina volume. A temperature of the reactor was raised to 150 to 310° C. while stirring, and heat treatment was performed by maintaining the temperature for 2 hours. A catalyst was prepared by cooling to room temperature.

A neutral alumina powder having a BET specific surface area of 150 to 250 $m^2/g$, an average particle size of 40 to 160 μm, and a pH of 7 under moisture was used. A basic alumina powder having a BET specific surface area of 150 to 250 $m^2/g$, an average particle size of 30 to 500 μm, and a pH of 9.5 under moisture was used. A neutral alumina ball having a BET specific surface area of 150 to 250 $m^2/g$, an average particle size of 0.8 to 1.2 mm, and a pH of 7 under moisture and having adjusted basicity by optional mixing with 0 to 2% by weight of NaOH based on a total catalyst content.

Experimental Example 2: Isomerization Reactor

A reaction in an isomerization reactor 410 according to reaction conditions was evaluated.

Experimental Example 2-1

The catalyst of Preparation Example 1 was charged into a tubular reactor. A 5-vinyl-2-norbornene raw material was supplied to the reactor filled with the catalyst at a space velocity of 4.5 $h^{-1}$. The reaction was performed at a temperature of 20° C. and 1 bar, and a product was analyzed by gas chromatography according to a reaction time.

In the case of using a purified 5-vinyl-2-norbornene raw material, one which was purified under conditions of a temperature of 70° C. and a pressure of 60 mbar using a vacuum distillation device and had a purity of 99.8% or more was used. When a purified raw material was used, the raw material was supplied to the tubular reactor while maintaining an inert gas atmosphere by supplying nitrogen, which is an inert gas, at a rate of 50 mL/min. An adsorbent was selectively mixed with the 5-vinyl-2-norbornene raw material to remove a polymerization inhibitor such as dibutylhydroxytoluene (BHT), cyclopentadiene, and reaction by-products.

A conversion rate over time was calculated using Equation 1 below, and the results are shown in Table 1 below.

$$\text{Conversion rate (mol \%)} = \{(\text{number of moles of 5-vinyl-2-norbornene supplied} - \text{number of moles of 5-vinyl-2-norbornene consumed})/\text{number of moles of 5-vinyl-2-norbornene supplied}\} \times 100 \quad [\text{Equation 1}]$$

TABLE 1

| Classification | NaOH (wt %) | Alumina type | Catalyst size (mm) | Raw material | Absorbent | Conversion rate after 1 hour (mol %) | Time to maintain 95% or higher conversion rate (h) |
|---|---|---|---|---|---|---|---|
| A | 2 | Neutral | 1 | Unpurified | Not used | 99.5 | 5 |
| B | 2 | Neutral | 1 | Unpurified | Used | 99.7 | 10 |
| C | 1 | Neutral | 1 | Unpurified | Used | 99.7 | 19 |
| D | 1 | Neutral | 1 | Purified | Not used | 99.7 | 18 |

TABLE 1-continued

| Classification | NaOH (wt %) | Alumina type | Catalyst size (mm) | Raw material | Absorbent | Conversion rate after 1 hour (mol %) | Time to maintain 95% or higher conversion rate (h) |
|---|---|---|---|---|---|---|---|
| E | 1 | Basic | — | Purified | Not used | 99.5 | 6 |
| F | 0 | Basic | — | Purified | Not used | 99.7 | 48 |

Referring to Table 1, A to D using neutral alumina as a support required basicity control using NaOH, and were prepared in a spherical to extruded shape of 1 mm and had excellent initial activity, but lacked stability. On the other hand, in the case of E, in which basicity was adjusted by inputting NaOH to basic alumina, catalytic activity was rather reduced. F, in which basic alumina was used without basicity control and the purified raw material was input under an inert gas atmosphere, had excellent catalytic activity and stability.

Referring to C, D, and F, even when neutral alumina was used to adjust basicity and an absorbent was used or raw material was purified to remove polymerization inhibitors and reaction by-products that may deactivate the catalyst, a conversion rate of 95 mol % or more was not maintained for 20 hours or more, but in the case of F using basic alumina, the conversion rate of 95 mol % or more was maintained for 48 hours or more, and stability was excellent.

Experimental Example 2-2

5.6 g of the catalyst of Preparation Example 1 and 400 g of purified 5-vinyl-2-norbornene were input to a batch reactor under an inert gas atmosphere. A reaction was performed by bubbling nitrogen at the bottom of a reactor at a rate of 200 mL/min, and a product was analyzed by gas chromatography according to a reaction time.

As a 5-vinyl-2-norbornene raw material, one which was purified under conditions of a temperature of 70° C. and a pressure of 60 mbar using a vacuum distillation device and had a purity of 99.8% or more was used. As the catalyst of Preparation Example 1, basic alumina powder was used, and NaOH was not input, and the heat treatment temperature was varied.

A conversion rate after 0.5 hours and a conversion rate after 20 hours in a batch process according to the heat treatment temperature during catalyst preparation were calculated, and the conversion rate after 20 hours in a continuous process of Experimental Example 2-1 was calculated, and the results were shown in Table 2 below.

TABLE 2

| Classification | | 150° C. | 190° C. | 220° C. | 250° C. | 280° C. | 310° C. |
|---|---|---|---|---|---|---|---|
| Experimental Example 2-2 (Batch) | Conversion rate after 0.5 hour (mol %) | 10.6 | 29.8 | 21.9 | 18.7 | 3.7 | 2.7 |
| | Conversion rate after 20 hours (mol %) | 38.5 | 92.8 | 93.1 | 94.2 | 12 | 7.9 |
| Experimental Example 2-1 (Continuous) | Conversion rate after 20 hours (mol %) | — | 99.7 | 99.7 | 72.6 | 55 | — |

Referring to Table 2, a catalyst heat-treated at 150° C. or lower or 280° C. or higher had an insufficient conversion rate. On the other hand, a catalyst heat-treated at 190 to 250° C. was excellent in both activity and stability, especially a catalyst heat-treated at 190 to 220° C. was excellent in stability in the continuous process.

Preparation Example 2: Isomerization Catalyst

After alumina powder (support) was input into a reactor, a temperature of the reactor was raised to 350° C. under an argon atmosphere and maintained for 2 hours. Thereafter, the reactor was cooled to a temperature ($T_1$) of 150° C. to 220° C., and sodium metal and/or sodium hydroxide was input thereto, and then stirred for 1 hour. Thereafter, the temperature of the reactor was raised to a temperature ($T_2$) of 150 to 310° C., maintained for 2 hours, and then cooled to room temperature to prepare a solid catalyst in powder form.

Specific preparation conditions of each catalyst are shown in Table 3 below, where a pH of an alumina support is the result of measuring a pH of a solution after mixing 5 g of the support and 45 g of distilled water and stirring for 30 minutes.

TABLE 3

| Classification | Alumina support | | | Sodium metal Content per unit volume of alumina support (g/mL) | Sodium hydroxide | | $T_1$ | $T_2$ |
|---|---|---|---|---|---|---|---|---|
| | pH | Average particle diameter (μm) | BET surface area (m²/g) | | Input amount based on total catalyst content (wt %) | pH of alumina support after input | | |
| A" | 7 | 120 | 200 | 0.12 | 2 | 10.7 | 150 | 220 |
| B" | 7 | 120 | 200 | 0.12 | 1 | 9.8 | 150 | 220 |
| C" | 9.5 | 120 | 200 | 0.12 | 1 | 10.9 | 150 | 220 |
| D" | 9.5 | 120 | 200 | 0.12 | 0 | 9.5 | 150 | 150 |
| E" | 9.5 | 120 | 200 | 0.12 | 0 | 9.5 | 150 | 190 |
| F" | 9.5 | 120 | 200 | 0.12 | 0 | 9.5 | 150 | 220 |
| G" | 9.5 | 120 | 200 | 0.12 | 0 | 9.5 | 150 | 250 |
| H" | 9.5 | 120 | 200 | 0.12 | 0 | 9.5 | 150 | 280 |

Experimental Example 3: Isomerization Reactor

A reaction in an isomerization reactor 410 according to reaction conditions was evaluated.

Experimental Example 3-1

The catalyst of Preparation Example 2 was charged into a tubular reactor. An inert gas atmosphere was maintained by supplying nitrogen, which is an inert gas, at a rate of 50 mL/min to a container filled with 5-vinyl-2-norbornene. A 5-vinyl-2-norbornene raw material was supplied at a space velocity of 4.5 h$^{-1}$. At this time, as the 5-vinyl-2-norbornene raw material, one which was purified under conditions of a temperature of 70° C. and a pressure of 60 mbar using a vacuum distillation device and had a purity of 99.8% or more was used. A reaction was performed at a temperature of 20° C. and 1 bar to obtain a product.

A conversion rate over time was calculated using Equation 1 below, and the results are shown in Table 4 below.

Conversion rate (mol %)={(number of moles of 5-vinyl-2-norbornene supplied−number of moles of 5-vinyl-2-norbornene consumed)/number of moles of 5-vinyl-2-norbornene supplied}*100  [Equation 1]

TABLE 4

| Classification | A" | B" | C" | D" | E" | F" | G" | H" |
|---|---|---|---|---|---|---|---|---|
| Conversion rate after 1 hour (mol %) | 99.5 | 99.7 | 99.5 | 95 | 99.7 | 99.7 | 99.7 | 91 |
| Conversion rate after 20 hours (mol %) | 86 | 95 | 85 | 62 | 99.7 | 99.7 | 72.6 | 55 |

Referring to Table 4, A" and B" using neutral alumina as a support required basicity control using NaOH, and had excellent initial activity, but lacked stability. Specifically, although B" showed basicity similar to that of the basic support, it did not show as much stability as when the basic support was used, and A", in which NaOH was additionally input to make basicity stronger, showed good initial activity of the catalyst, but significantly reduced stability. In addition, even in the case of C" in which basic alumina was used as a support, but basicity was adjusted by inputting NaOH, initial activity was good, but stability was found to be reduced. D", which had an excessively low heat treatment temperature after mixing the catalyst and the basic support, showed weak initial activity as well as weak stability due to an insufficient bonding force between the support and an active material, and G" and H", which had an excessively high heat treatment temperature after mixing the catalyst and the basic support, showed that the catalyst penetrated deeply into the basic support and stability was remarkably deteriorated.

In contrast, E" and F", in which basic alumina was used without basicity adjustment and the heat treatment temperature was properly adjusted after mixing the catalyst and the basic support, were found to stably maintain excellent catalytic activity.

Experimental Example 3-2

In order to evaluate a conversion rate according to a reaction temperature, 10 mL of catalyst F" prepared in Preparation Example 2 was introduced into a ½" tubular reactor, and the conversion rate according to the reaction temperature was observed while supplying a 5-vinyl-2-norbornene raw material at a space velocity of 3 h$^{-1}$ under a condition of 1 bar. The results are shown in FIG. 2.

Figure 2:
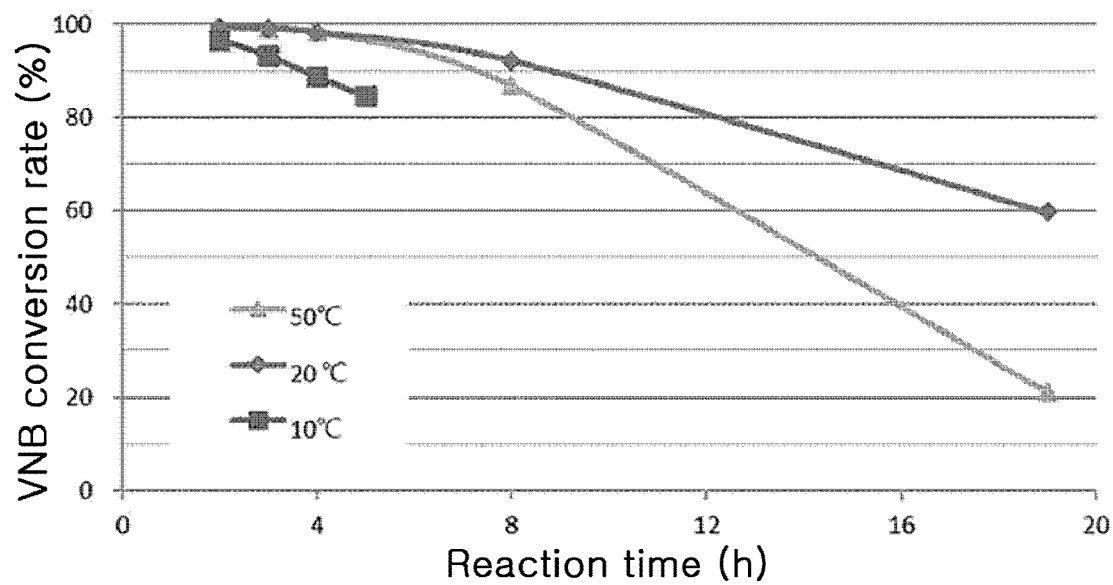
FIG. 2 shows a measurement of a conversion rate of reactants according to a reaction temperature in preparation of 5-ethylidene-2-norbornene using a catalyst prepared according to a preparation example of the present specification.

Referring to FIG. 2, in the case of a reaction temperature of 20° C., the conversion rate and stability were the best. In contrast, at 50° C. and 10° C., it could be confirmed that reaction by-products were excessively prepared, respectively, or the by-products were easily adsorbed on the catalyst surface, and stability was lowered.

Experimental Example 3-3

In order to evaluate a conversion rate according to a space velocity of raw materials, Catalyst F" prepared in Preparation Example 2 was input into a ⅜" or ½" tubular reactor, and a conversion rate according to the space velocity of the raw material was observed while supplying a 5-vinyl-2-norbornene raw material at a temperature of 20° C. and 1 bar. The results are shown in Table 5 below and (a) and (b) of FIG. 3.

Volume multiple=raw material feed rate $X$ conversion rate retention time/catalyst volume  [Equation 2]

TABLE 5

| Classification | Reactor diameter (inch) | Catalyst volume (mL) | Raw material feed rate (mL/min) | Space velocity ($h^{-1}$) | Linear velocity (cm/min) | 99% reference volume multiple (raw material/catalyst) | Retention time of conversion rate of 99% or more |
|---|---|---|---|---|---|---|---|
| A' | 3/8 | 5 | 0.125 | 1.5 | 0.325 | 317 | 211 |
| B' | 3/8 | 5 | 0.375 | 4.5 | 0.974 | 149 | 33 |
| C' | 3/8 | 15 | 0.375 | 1.5 | 0.974 | 258 | 172 |
| D' | 1/2 | 15 | 0.25 | 1 | 0.312 | 500 | 500 |

Figure 3:
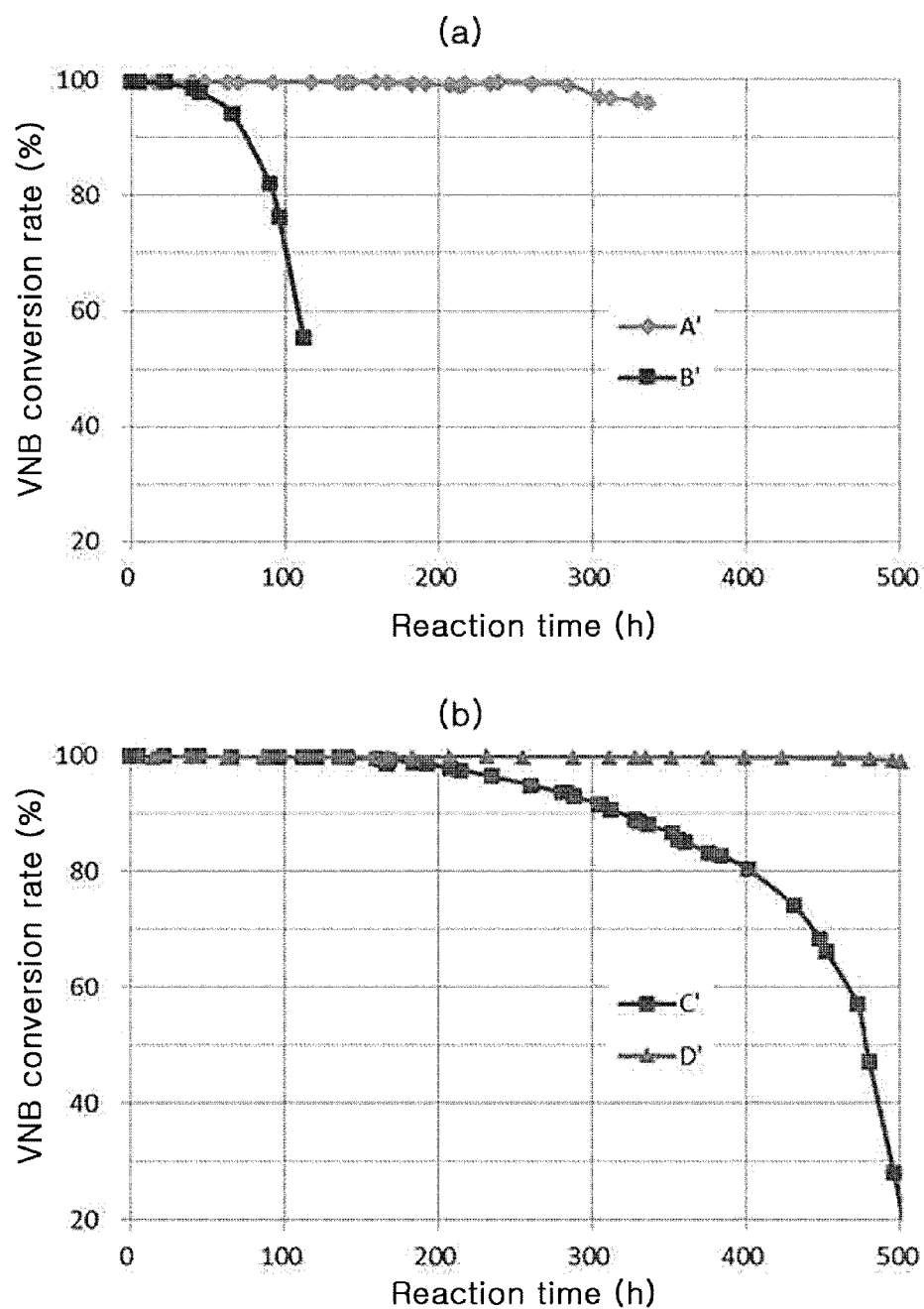
FIG. 3 shows a measurement of a conversion rate of reactants according to movement velocity of raw materials in preparation of 5-ethylidene-2-norbornene using a catalyst prepared according to a preparation example of the present specification.

Referring to Table 5 and (a) and (b) of FIG. 3, when a feed rate of the raw material in A' and B' of the same reactor and the same catalyst volume increased, the inactivation factor increased and stability decreased. It can be seen that A' has a lower space velocity and linear velocity compared to B', and thus has excellent catalytic activity and an excellent catalytic lifetime. In A' and C' of the same reactor and the same space velocity, it can be confirmed that C' has a higher linear velocity than A', so that stability is lowered, and a conversion rate according to a reaction time is rapidly lowered after 300 hours. Accordingly, it can be confirmed that a low linear velocity is advantageous for catalytic activity and stability when the space velocity is the same. Referring to B' and C', it can be confirmed that the time to maintain the same conversion rate increases as the catalyst volume increases in the same reactor and at the same feed rate of the raw material. That is, it can be confirmed that a low space velocity is advantageous for catalytic activity and stability when the linear velocity is the same. Referring to A' and D', it can be confirmed that catalytic activity and stability are excellent when the diameter of the reactor is increased even when a feed rate of the raw material is increased. In particular, in the case of D', the conversion rate and stability according to the reaction time were the best.

Preparation Example 3: Isomerization Catalyst Slurry

A solid catalyst of Preparation Example 2 was input into at least one solvent selected from the group consisting of heptane, toluene, and paraffin oil to prepare a solid catalyst slurry.

Experimental Example 4: Isomerization Reactor

In order to evaluate an isomerization conversion rate according to the type of solvent, a solid catalyst slurry of Preparation Example 3 was filled into a tubular reactor. As a comparative example, a reaction was performed by setting a solid catalyst not supported in a solvent. Nitrogen, which is an inert gas, was supplied to the reactor filled with the solid catalyst slurry or the solid catalyst at a rate of 50 mL/min to maintain an inert gas atmosphere. A 5-vinyl-2-norbornene raw material was supplied at a space velocity of 4.5 $h^{-1}$. At this time, as the 5-vinyl-2-norbornene raw material, one which was purified under conditions of a temperature of 70° C. and a pressure of 60 mbar using a vacuum distillation device and had a purity of 99.8% or more was used. A reaction was performed at a temperature of 20° C. and 1 bar to obtain a product, and the results are shown in FIG. 4.

Figure 4:
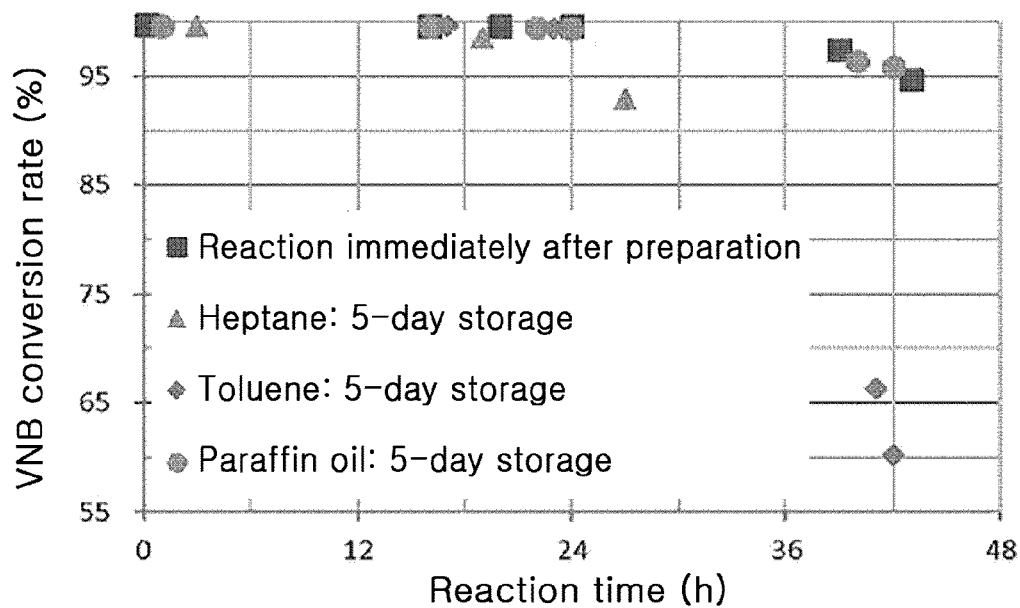
FIG. 4 shows a measurement of a conversion rate of reactants according to a slurry solvent in preparation of 5-ethylidene-2-norbornene using a catalyst prepared according to a preparation example of the present specification.

Referring to FIG. 4, the solid catalyst of the comparative example reacted immediately after preparation, and showed a conversion rate of 95% or more for 42 hours. As seen from the results of a reaction with respective catalysts in which the solid catalyst slurry of Preparation Example 3 was stored in heptane, toluene, and paraffin oil for 5 days, it can be confirmed that when the reaction was performed with the catalyst slurry stored in heptane for 5 days, the conversion rate was 95% or less after 24 hours, and in the case of the catalyst slurry stored in toluene for 5 days, stability was improved compared to storage in heptane, but the conversion rate at 42 hours was rapidly reduced. In the case of the catalyst slurry stored in paraffin oil for 5 days, it can be confirmed that a conversion rate similar to that of the comparative example can be achieved by exhibiting a conversion rate of 95% or more for 42 hours.

However, the solid catalyst of the comparative example was filled into a reactor immediately after preparation and reacted with 5-vinyl-2-norbornene to show an excellent conversion rate, and in storage at room temperature, activity may decrease due to contact with air or moisture, so that it can be predicted that storage stability will decrease. In the case of the solid catalyst slurry of Preparation Example 3, it can be predicted that since it is prepared in the form of a slurry using a solvent, it has excellent storage stability and can prevent activity deterioration caused by storage, transfer, and reaction processes.

Experimental Example 5: Isomerization Catalyst Disposal

Figure 5:
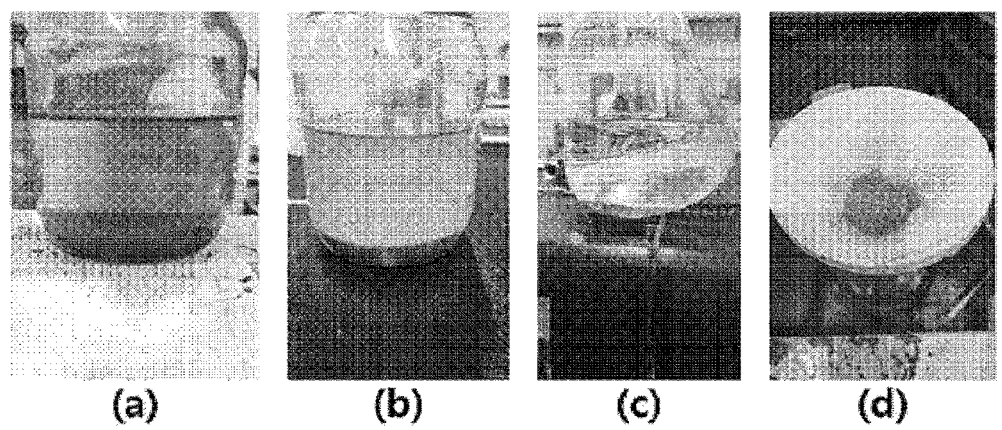
FIG. 5 shows a process in which a catalyst prepared according to a preparation example of the present specification is discarded after completion of the reaction.

After the completion of an isomerization reaction, an experiment was performed to safely dispose of a spent catalyst, and the progress is shown in FIG. 5.

Referring to (a) of FIG. 5, after the reaction was completed, 5 mL of the spent catalyst separated from the reactants and products by a nitrogen purge was input into a separate container containing 150 mL of toluene to prepare a spent catalyst slurry. Referring to (b) of FIG. 5, while stirring the container, 2 mL of water was input dividedly twice or more, and gas produced while oxidizing the catalyst was exhausted, and it can be seen that inputting and stirring of water were maintained until no additional bubble formation occurred, and a completely oxidized spent catalyst precipitated to the bottom of the container. Referring to (c) of FIG. 5, it is shown that toluene and water in a separated state from the spent catalyst are layered, and referring to (d) of FIG. 5, it can be confirmed that a separated spent catalyst is safely separated and discarded.

Advantageous Effects

A preparation process of 5-ethylidene-2-norbornene according to one aspect of the present specification can have excellent separation/purification efficiency in each process, use less utilities compared to conventional processes, and improve the efficiency and economics of the entire process by minimizing process trouble and raw material loss.

The effect of one aspect of the present specification is not limited to the above-described effect, and it should be understood to include all effects that can be inferred from the configuration described in the detailed description or claims of the present specification.

The description of the present specification described above is for illustration, and it should be understood that those of ordinary skill in the art to which one aspect of the present specification belongs can easily modify it into other specific forms without changing the technical idea or essential features described in this specification. Therefore, it should be understood that the embodiments described above are illustrative in all respects and not restrictive. For example, each component described as a single type may be implemented in a distributed form, and likewise components described as distributed may be implemented in a combined form.

The scope of the present specification is indicated by the following claims, and all changes or modifications derived from the meaning and scope of the claims and their equivalents should be construed as being included in the scope of the present specification.

What is claimed is:

1. A preparation process of 5-ethylidene-2-norbornene, comprising:
    step a-1 of introducing dicyclopentadiene (DCPD) into a DCPD decomposition reactor (110) to thermally decompose the DCPD, wherein the DCPD decomposition reactor includes a thermal decomposition reaction portion adjusted to a temperature of 300 to 500° C.;
    step a-2 of introducing a product of the step a-1 into a cyclopentadiene (CPD) purification tower (120);
    step b-1 of introducing 1,3-butadiene (BD), a solvent, and cyclopentadiene separated from a top of the CPD purification tower (120) into a Diels-Alder reactor (210) to react the same, wherein the solvent has a boiling point of 70 to 140° C.;
    step b-2 of introducing a product of the step b-1 into a BD removal tower (220) to recover 1,3-butadiene from the top thereof;
    step b-3 of introducing a mixture at a bottom of the BD removal tower (220) into a desolvation tower (230) to recycle the solvent and unreacted raw materials recovered from a top of the desolvation tower (230) to the DCPD decomposition reactor (110);
    step c of introducing a mixture at a bottom of the desolvation tower (230) into a 5-vinyl-2-norbornene (VNB) separation tower (300) to separate 5-vinyl-2-norbornene; and
    step d of introducing the 5-vinyl-2-norbornene into an isomerization reactor (410) to react the same.

2. The process of claim 1, wherein the VNB separation tower (300) includes a first VNB separation tower (310) and a second VNB separation tower (320), and
    the step c comprises:
    step c-1 of introducing the mixture at the bottom of the desolvation tower (230) into the first VNB separation tower (310) to introduce a mixture separated from a top of the first VNB separation tower (310) into the second VNB separation tower (320); and
    step c-2 of separating 5-vinyl-2-norbornene from a bottom of the second VNB separation tower (320).

3. The process of claim 2, wherein the mixture separated from the top of the first VNB separation tower (310) includes 5-vinyl-2-norbornene and 4-vinyl-cyclohexene (VCH).

4. The process of claim 3, wherein the 4-vinyl-cyclohexene is separated from the top of the second VNB separation tower (320).

5. The process of claim 2, further comprising step e of introducing a mixture at a bottom of the first VNB separation tower (310) into a DCPD recovery tower (510) to recycle materials recovered from a top of the DCPD recovery tower (510) into the DCPD decomposition reactor (110).

6. The process of claim 5, wherein the materials recovered from the top of the DCPD recovery tower (510) includes dicyclopentadiene and 3a,4,7,7a-tetrahydroindene (THI).

7. The process of claim 6, wherein the 3a,4,7,7a-tetrahydroindene is separated from a bottom of the CPD purification tower (120).

8. The process of claim 1, wherein the step a-1 is a step of introducing dicyclopentadiene into the DCPD decomposition reactor (110) and thermally decomposing the dicyclopentadiene in the presence of an inert gas.

9. The process of claim 1, wherein in the step b-1, a molar ratio of cyclopentadiene and 1,3-butadiene introduced into the Diels-Alder reactor (210) ranges from 1:2 to 1:4.

10. The process of claim 1, wherein the step d comprises:
    step d-1 of filling the isomerization reactor (410) with a catalyst; and
    step d-2 of introducing the 5-vinyl-2-norbornene into the isomerization reactor (410) to react the 5-vinyl-2-norbornene.

11. The process of claim 10, wherein the catalyst is a catalyst in which an alkali metal or alkaline earth metal is supported on a surface of a basic support.

12. The process of claim 10, wherein the catalyst is a solid catalyst prepared by a method comprising:
    step 1 of heat-treating a basic support;
    step 2 of mixing the heat-treated basic support with an alkali metal or alkaline earth metal to obtain a mixture; and
    step 3 of heat-treating the mixture.

13. The process of claim 12, wherein the catalyst is a solid catalyst slurry prepared by a method further comprising step 4 of inputting the solid catalyst into at least one solvent selected from the group consisting of heptane, toluene, and paraffin oil.

14. The process of claim 12, wherein the basic support satisfies at least one of the following conditions (i) to (iii):
    (i) a pH of 8.5 to 11;
    (ii) an average particle diameter of 30 to 500 μm; and
    (iii) a BET specific surface area of 150 to 250 m$^2$/g.

15. The process of claim 12, wherein the step 1 is performed at 150 to 500° C., the step 2 is performed at a temperature of 20 to 80° C. or more compared to a melting point ($T_m$) of the alkali metal or alkaline earth metal, and the step 3 is a performed at a temperature of 50 to 150° C. or more compared to the melting point ($T_m$) of the alkali metal or alkaline earth metal.

16. The process of claim 12, wherein a weight of the alkali metal or alkaline earth metal relative to a volume of the basic support is 0.05 to 0.5 g/mL.

17. The process of claim 12, wherein the steps 1 to 3 are performed under conditions of an oxygen concentration of 100 ppm or less.

18. The process of claim 10, wherein a temperature of the isomerization reactor (410) in the step d-2 is maintained at 10 to 50° C., and
    a space velocity of the 5-vinyl-2-norbornene is 5.0/h or less.

19. The process of claim 18, wherein the space velocity of the 5-vinyl-2-norbornene is 2.0/h or less.

20. The process of claim 10, wherein the step d further comprises:
- step d-3 of inputting a spent catalyst used in the reaction into at least one solvent selected from the group consisting of heptane, toluene, and paraffin oil to obtain a spent catalyst slurry; and
- step d-4 of inputting water to the spent catalyst slurry to oxidize the catalyst.

* * * * *